United States Patent
Yamashita

(10) Patent No.: US 6,187,326 B1
(45) Date of Patent: *Feb. 13, 2001

(54) SOIL AMENDMENT COMPOSITION

(76) Inventor: Thomas T. Yamashita, 3631 Bogue Rd., Denair, CA (US) 95316-9619

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/222,459

(22) Filed: Dec. 29, 1998

(51) Int. Cl.$^7$ .......................... A01N 25/00; A01N 63/00; A61K 35/00; C05G 3/00; C05G 3/02

(52) U.S. Cl. ..................................... 424/405; 71/1; 71/11; 71/903; 424/116; 504/101; 504/113; 504/116; 504/118

(58) Field of Search .................................. 71/1, 11, 903; 424/405, 116; 504/101, 113, 116, 118

(56) References Cited

U.S. PATENT DOCUMENTS

| | | | |
|---|---|---|---|
| 5,549,729 | 8/1996 | Yamashita | 71/26 |
| 5,582,627 | 12/1996 | Yamashita | 71/26 |
| 5,696,094 | 12/1997 | Yamashita | 514/22 |
| 5,797,976 | 8/1998 | Yamashita | 71/26 |

*Primary Examiner*—David M. Naff
*Assistant Examiner*—Deborah K. Ware
(74) *Attorney, Agent, or Firm*—Bret E. Field; Bozicevic, Field & Francis

(57) ABSTRACT

Soil amendment compositions and methods for using the same are provided. The subject compositions are aqueous compositions consisting essentially of a carbon-skeleton energy component, a predisposing agent and a vitamin-cofactor component. The subject compositions find use in a variety of soil amendment applications, including: the control of soil born pests and pathogens; the improvement in soil fertility and/or characteristics, e.g. mineral release, water filtration; the neutralization and/or degradation of toxins, etc. Further, an aqueous composition containing 10 to 50% w/w of a molasses and lignosulfonate, as well as 0.001 to 10% w/w of gallic acid and a yeast extract is also disclosed. In addition, the composition does not include nitrogen, phosphorous, zinc, iron or manganese.

19 Claims, No Drawings

SOIL AMENDMENT COMPOSITION

INTRODUCTION

1. Field of the Invention

The field of the invention is agriculture, particularly fertilizers.

2. Background

In agriculture, it is often desirable to use land that is not initially optimal in terms of soil fertility. Fertilizers have been developed for use on such land. Fertilizers are materials that are used to supply elements needed for plant nutrition. Fertilizer materials may be in the form of solids, semi-solids, slurry suspensions, pure liquids, aqueous solutions and gases. Fertilizing materials may be introduced into a plant's environment in a number of different ways, including through addition to the soil, through application directly to a plant's foliage, and the like. The use of fertilizers is critical to commercial agriculture as fertilizers are essential to correct natural deficiencies and/or replace components in soil. A number of different types of fertilizer compositions have been developed and employed in agriculture. However, there is continued interest in the development of new fertilizer compositions.

Another problem encountered by farmers and other agricultural workers is soil infestation with deleterious pests and/or pathogens. A variety of synthetic chemical pesticides have been developed over the years to treat pest or pathogen infested soils. While such synthetic chemicals have been used with success, their use is not without controversy. Specifically, there is increasing public concern over the potential link between pesticide use and human disease conditions. As such, there is continued interest in the identification of new compositions which are capable of controlling soil borne pests or pathogens.

Relevant Literature

U.S. Pat. Nos. of interest include:5,549,729; 5,582,627; 5,696,094; 5,797,976; the disclosure of which are herein incorporated by reference.

SUMMARY OF THE INVENTION

Soil amendment compositions and methods for their use are provided. The subject compositions are aqueous compositions that include a predisposing agent, a carbon-skeleton-energy component and a vitamin-cofactor component. The subject compositions find use in a variety of different applications, including: the control of soil borne pests or pathogens; the neutralization and/or degradation of toxins; the improvement of soil characteristics, e.g. water permeability; the improvement of soil fertility; etc.

DESCRIPTION OF THE SPECIFIC EMBODIMENT

Aqueous compositions and methods for their use in soil amendment applications are provided. The subject compositions include a predisposing agent, a carbon-skeleton-energy (CSE) source and a vitamin co-factor component. The subject compositions find use in a variety of different soil amendment applications, where such applications include: reducing the population of soil borne pests or pathogens; neutralizing or degrading soil toxins; improving soil characteristics; improving soil fertility; and the like. In further describing the invention, the compositions are described first in greater detail followed by a discussion of representative soil amendment methods in which the subject compositions find use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

A critical component of the subject aqueous compositions is the predisposing agent. By predisposing agent is meant an agent which can traverse the membranes of a target pest or pathogen and thereby weaken the pest or pathogen physiology by virtue of denaturation of key enzymes (e.g. cytochrome oxidase) and/or proteins, and the like. A variety of different compounds are capable of fulfilling the above functional requirements and thereby serving as predisposing agents. As such, predisposing agents of interest include: aromatic amino acids, e.g. tyrosine, phenylalanine, tryptophan; phenols and derivatives and general products or reactants of the Shikimic Acid Pathway, e.g. cinnamic acid, chlorogenic acid, caffeic acid, coumaric acid, catechuic acid, ferulic acid, chorismic acid, quinic acid, gallic acid, gallotannins, scopeletin, dicoumarol, preocenes, phytoalexins such as orchinol, phaseolin, pisatin, isocoumarin, and the like; lignin alcohols e.g. coniferyl, sinapyl, p-coumaryl; flavonoids e.g. cyanidin, anthocyanidin, pelargonidin, delphinidin, malidin, peonidin, petunidin; flavonols and flavones; betalains e.g. betacyanin, betalain, betaxanthin; alkaloids e.g. caffeine, nicotine, theobromine; limonene-1-Methyl-4-(1-Methylethenyl) cyclohexene; p-mentha-1,8-diene; lignosulfonates, e.g. calcium lignosulfonate, potassium lignosulfonate, sodium lignosulfonate, ammonium lignosulfonate; and the like.

The subject compositions may include a single predisposing agent or a plurality of different predisposing agents. When a plurality of different predisposing agents are employed, the number of different predisposing agents may range from about 2 to 6, usually from about 2 to 5 and more usually from about 2 to 4.

The total amount of predisposing agent(s) that is present in the subject compositions is sufficient to achieve the desired weakening in the target pest or pathogen present in the soil. Generally, the amount present in the composition is sufficient to achieve a concentration in the soil following treatment ranging from about 5 to 650 ppm, usually from about 10 to 350 ppm and more usually from about 25 to 200 ppm. The amount of predisposing agent present in the composition may vary depending on whether the composition is to be applied "as is" to the soil or diluted prior to application, e.g. where the composition is a concentrate, as described infra. However, in many embodiments, the total amount of predisposing agent present in the composition ranges from about 5 to 75, usually from about 10 to 60 and more usually from about 15 to 60% w/w of the composition.

A particularly preferred predisposing agent in many embodiments of the invention is a lignosulfonate. Lignosulfonates of interest include: calcium lignosulfonate, potassium lignosulfonate, sodium lignosulfonate, ammonium lignosulfonate; and the like. The lignosulfonate is generally present in the composition in an amount that is sufficient to achieve a concentration in the soil following application that ranges from about 5 to 650 ppm, usually from about 10 to 350 ppm and more usually from about 25 to 200 ppm. In many embodiments, the amount of lignosulfonate present in the composition ranges from about 5 to 75% w/w, usually from about 10 to 50% w/w and more usually from about 15 to 60% w/w or 30 to 40% w/w of the composition. Lignosulfonates are generally available from Westway Terminal, Stockton Calif.; PM Ag, Stockton Calif.; Georgia Pacific, Bellingham Wash.; and the like.

Also of particular interest as a predisposing agent is gallic acid. When present, gallic acid is present in an amount sufficient to achieve a soil concentration ranging from about 0.05 to 5.0 ppm, usually from about 0.1 to 5.0 ppm and more usually from about 0.2 to 1.0 ppm. In many embodiments, the amount of gallic acid present in the composition ranges from about 0.001 to 15% w/w, usually from about 0.001 to 10% w/w and more usually from about 0.01 to 10% w/w.

In a particularly preferred embodiment, the subject soil amendment compositions include both a lignosulfonate and gallic acid. In such embodiments, the amounts of each of these agents in the composition are sufficient to achieve a lignosulfonate concentration in the treated soil that ranges from about 10 to 650 ppm and a gallic acid concentration in the soil that ranges from about 0.05 to 5.0 ppm. In many compositions falling within the scope of this preferred embodiment, the amount of lignosulfonate ranges from about 10 to 50% w/w of the composition while the amount of gallic acid ranges from about 0.001 to 10% w/w of the composition.

A second critical component of the subject compositions is the carbon-skeleton-energy (CSE) component. CSE components that find use in the subject compositions are carbon containing substances which provide a readily assimilable source of both carbon and energy for promoting microbial proliferation. Preferably, the CSE component provides a complex array of various carbon compounds such that varied enzymology is induced in microbes present in the target soil. As such, CSE sources that favor ancestral, beneficial species, which normally carry complex enzyme systems (as opposed to more simplified forms hosted by facultative pathogens) are particularly preferred. Generally, the carbon-skeleton-energy component is a $C_2$ to $C_{10}$, usually $C_4$ to $C_8$ compound or polymer thereof, e.g. a polymer in which the monomeric units are $C_2$ to $C_{10}$ compounds, such as a polysaccharide. The CSE component may be a single carbon containing compound or a composition of two or more different carbon containing or organic compounds. Compounds and compositions capable of serving as a CSE component include: complex organic compositions, such as molasses (e.g. cane, sugar beet, sorghum, etc.), whey, corn steep liquor, grape syrup, maple syrup, corn syrup, etc; sugars, e.g. sucrose, fructose, glucose, lactose, galactose, dextrose, maltose, raffinose, ribose, ribulose, xylulose, xylose, amylose, arabinose, etc.; sugar phosphates, e.g. fucose-P, galactose-P, glucose-P, lactose-P, maltose-P, mannose-P, ribose-P, ribulose-P, xylose-P, xylulose-P, etc.; sugar alcohols, e.g. adonitol, sorbitol, mannitol, maltitol, ribitol, galactitol, glucitol, etc.; organic acids, e.g. gluccuronic acid, alpha ketoglutaric acid, galactonic acid, glucaric acid, gluconic acid, pyruvic acid, polygalacturonic acid, citric acid, succinic acid, malic acid, isocitric acid, folic acid, etc.; nucleotides and bases, e.g. adenosine, adenosine-P, uridine, uridine-P, thymine, thymine-P, cytosine, cytosine-P, guanine, guanine-P, etc.; and amino acids, e.g. glycine, alanine, leucine, isoleucine, asparagine, tyrosine, phenylalanine, serine, cysteine, valine, proline, methionine, glutamine, threonine, lysine, aspartic acid, glutamic acid, arginine, and the like.

The CSE component is present in an amount sufficient to provide for a concentration in the target soil upon application that ranges from about 5 to 650 ppm, usually from about 10 to 350 ppm and more usually from about 25 to 200 ppm. In many embodiments, the amount of CSE component in the composition ranges from about 5 to 75% w/w, usually from about 10 to 50% w/w and more usually from about 15 to 60% w/w or 30 to 40% w/w of composistion.

In a preferred embodiment, the CSE source is a molasses. Molasses may be obtained from a number of commercial sources, including cane molasses, etc., where commercial sources of molasses include: Westway Terminal, Stockton Calif.; PM Ag, Stockton, Calif.; and the like.

The final component is a vitamin-cofactor. A variety of agents are capable of serving as the vitamin-cofactor component of the subject aqueous compositions. Such agents include: yeast extract, yeast, vitamin Bs, e.g. thiamine pyrophosphate, riboflavin, biotin, pantothenic acid, phosphatidylcholine, inositol, PABA, nicotinic acid, folic acid and mixtures thereof, and the like. Of particular interest as a vitamin-cofactor is yeast extract, particularly yeast extract obtained from spray dried extract, as available from Feedstuffs, Inc., Stockton Calif.; California Spray Dry, Stockton, Calif.; and the like. The amount of vitamin-cofactor component present in the composition is sufficient to provide a concentration in the treated soil that ranges from about 0.01 to 10 ppm, usually from about 0.01 to 5.0 ppm and more usually from about 0.01 to 1 ppm. The amount of vitamin co-factor present in the composition generally ranges from about 0.001 to 15% w/w, usually from about 0.001% to 10% w/w and more usually from about 0.01 to 5.0% w/w or 2 to 5% w/w of the composition.

Importantly, the composition includes substantially no macronutrients, e.g. nitrogen, potassium, phosphorous; or micronutrients, e.g. zinc, iron or manganese. By "substantially no" is meant that the amount of any one of these elements, if present in the composition, is insufficient for the element to influence the overall activity of the composition or the amendment of the target soil, i.e. the amount of the component is insufficient to make the component an active ingredient of the composition. As such, for nitrogen, phosphorous and potassium, the amount present in the composition, if present at all, does not exceed about 5% and preferably does not exceed about 2.5%. For iron, zinc and manganese, the amount present in the composition, if present at all, does not exceed about 2% and preferably does not exceed about 1%. Despite the lack of these macro- and micronutrients, the composition exhibits significant soil amendment activity.

As the subject compositions are aqueous compositions, they further include a substantial amount of water. The amount of water present in the composition may vary depending on whether the composition is a concentrated or dilute composition. Generally, the compositions include at least about 5%, usually at least about 20% and more usually at least about 30% water, where the amount of water present in the composition may be as high as 80% or higher, but generally does not exceed about 70% and usually does not exceed about 40%.

The above soil amendment compositions are prepared by combining water with the various agents under conditions sufficient to produce an aqueous solution containing the various agents. The water that is used to produce the subject compositions may be tap water obtained from any convenient water source, e.g. a municipal water district, where the water may be purified or otherwise treated, e.g. to remove certain undesirable agents that may be initially present therein. The various agents to be solubilized in the water to produce the soil amendment compositions may be obtained from any convenient source, e.g. commercial vendor. For example, the carbohydrate component may be derived from a commercially available carbohydrate source, such as commercially available molasses, etc.

In preparing the subject soil fertilizer compositions, a concentrated or parent composition may first be produced, which parent composition or mix may or may not be diluted with water.

The subject aqueous compositions find use in a variety of soil amendment applications, i.e. methods of improving soil. In practicing the subject methods, the aqueous composition is contacted with the soil under conditions sufficient to achieve the desired concentrations of the agents of the composition in the soil. By contact is meant that the composition is introduced into the soil such that the desired concentration of the disparate components of the composition is obtained in the soil. As such, contact can include spraying so that the composition soaks into the soil, injecting the composition into the soil, flooding the soil with the composition, and the like. Contact is performed such that the concentration in the soil of the predisposing agent following treatment is at least about 5 ppm, usually at least about 20 ppm and more usually at least about 60 ppm, where the concentration of the predisposing agent following treatment may be as high as 650 ppm or higher, but generally does not exceed about 200 ppm and usually does not exceed about 60 ppm. Contacting also results in a concentration of the CSE component in the soil that is at least about 5 ppm, usually at least about 20 ppm and more usually at least about 60 ppm, where contact may result in a concentration of the CSE component that is 650 ppm or higher, but generally does not exceed about 200 ppm and usually does not exceed about 60 ppm. In addition, contact of the composition with the soil results in a vitamin-cofactor concentration in the soil that is at least about 0.01 ppm, usually at least about 0.05 ppm and more usually at least about 1.0 ppm, where the vitamin-cofactor concentration may be as high as 10 ppm or higher, but generally does not exceed about 5.0 ppm and usually does not exceed about 1.0 ppm.

The amount of aqueous composition that is used during any one application will vary greatly depending on the nature of the soil, the nature of the composition, the environmental conditions, etc. Where crops are treated with the subject compositions, the amount that is applied based on treated acreage is generally at least about 5 to 240 gal per acre, usually at least about 10 to 120 gal per acre, and more usually at least about 20 to 60 gal per acre, where the amount that is applied may be as high as 480 gal per acre or higher, but will usually not exceed about 240 gal per acre.

Depending on the nature of the soil, the nature of the composition, and the environmental conditions, as well as other factors, the composition may be applied more than once over a given period of time. As such, the composition may be applied daily, weekly, every two weeks, monthly etc.

The aqueous compositions of the subject invention find use in a variety of different applications, where such applications include: the control of soil borne pests and pathogens; the improvement of water filtration; the improvement in mineral release; the enhancement in the water holding capacity of soil; the mellowing of soil textural qualities; the enhancement of the decomposition of plant tissues and accelerated degradation of potentially toxic chemicals and/or allelopathic chemicals; the improvement of root mass in plants grown in treated soil; and the like.

A variety of different soil borne pests may be controlled with the subject compositions. Such pests include: plant parasitic nematodes, phylloxera, grubs, and the like. By contolled is meant that the pest population in the soil is reduced, generally by at least about 5%, usually at least about 25% and more usually at least about 50%. As such, the invention provides methods and compositions for at least reducing, if not substantially eliminating, the population of soil borne pests in soil.

Similarly, the subject methods and compositions provide means for reducing the amount of pathogen present in soil. Pathogens that can be targeted with the subject methods include: pathogenic fungi, actinomycetes, bacteria, viruses, and the like. The subject methods result in a reduction of at least about 5%, usually at least about 25%, and more usually at least about 50% of the amount of pathogen in the soil.

Also provides by the subject invention are methods and compositions for increasing indigenous soil microbe populations. Beneficial microbes whose population may be increased by the subject invention include: bacteria, fungi, actinomycetes, various free-living invertebrates, and the like. Applying the composition to the soil according to the subject methods results in at least a 2-fold increase, usually at least about a 20-fold increase and more usually at least about 40-fold increase in the microbe population in the treated soil.

The subject methods and compositions can also be used to improve water filtration through the soil. Water filtration may be improved by at least about 1.5×, usually at least about 2.5× and more usually at least about 4.5×.

Soil mineral release can also be enhanced using the subject methods and compositions. Mineral release, e.g. the release of minerals such as calcium, potassium and phosphorous, can be improved by at least about 1.5×, usually at least about 3.0× and more usually at least about 5.0× as compared to that observed in control soil.

Finally, the subject methods and compositions can be used to increase the root mass of plants grown in the treated soil. Generally, the subject methods result in an increase in root mass of at least about 1.5×, usually at least about 2.0× and more usually at least about 4.0×, as compared to control plants, i.e. plants grown in untreated but otherwise substantially identical soil.

The following experiments are offered by way of illustration and not by way of limitation.

EXPERIMENTAL

I. Tests to Indicate Efficacy of Various Predisposing Agents

The merits of alternative predisposing agents were examined by subjecting J2 larvae of the Root Knot Nematode (*Meloidogyne incognita*) to solutions of lignosulfonate and gallic acid. J2 larvaewere exposed 24 hours to various concentrations of the materials in shallow 50 ml beakers. Following exposure, nematodes were inspected for activity level using touch response:

| Treatment | 1 | 2 | 3 | 4 | Total | Mean | Control % |
|---|---|---|---|---|---|---|---|
| 1000 ppm Ligno | 256/452 | 262/460 | 235-/445 | 245/490 | 998/1847 | 250/462 | 45.9% |
| 5 ppm Gal Ac | 305/462 | 316/440 | 326/447 | 302/450 | 1249/1799 | 312/450 | 30.7% |
| 25 ppm Gal Ac | 250/458 | 248/449 | 232/459 | 225/462 | 955/1828 | 239/457 | 47.7% |

-continued

| Treatment | 1 | 2 | 3 | 4 | Total | Mean | Control % |
|---|---|---|---|---|---|---|---|
| 100 ppm Gal Ac | 193/450 | 185/448 | 176/436 | 150/464 | 704/1798 | 176/450 | 60.9% |
| 1000 ppm Gal Ac | 25/449 | 39/444 | 40/454 | 27/460 | 131/1807 | 33/452 | 92.7% |

Ligno = Ca Lignosulfanate
Gal Ac = Gallic Acid
Numbers listed are the active, responding nematodes per total examined (viable/total)

II. Compositions

Two amendment compositions were prepared: (a) an enhanced composition; and (b) a standard composition.

A. Enhanced (Enh) Composition Utilized

| Component | Material Source | Amount % w/w | Final Concentration of a.i. in Total Mix |
|---|---|---|---|
| Carbon Skeleton-Energy (CSE) | Hi-Brix Molasses | 35% | 17.5% CSE |
| Predisposing Agent | Ca Lignosulfonate | 35% | 17.6% Predisp. Agent |
|  | Gallic Acid | 0.10% |  |
| Vitamin-Cofactor | Yeast Extract | 2.5% | 1.3% Vit-Cofactor |
| Water | Tap Water | 27.5% | 27.5% Water |

Hi-Brix Molasses obtained from Westway Terminal, Stockton, CA
CaLignosulfonate obtained from Georgia-Pacific
Gallic Acid obtained from Sigma Chemical Company
Yeast Extract obtained from Sigma Chemical Company

B. Standard (Std) Composition Utilized

| Component | Material Source | Amount % w/w | Final Concentration of a.i. in Total Mix |
|---|---|---|---|
| CSE | Hi Brix Molasses | 32% | 16.0% CSE |
| Complexing Agent | Ca Lignosulfonate | 32% | 16.0% Cplx |
| Nitrogen | Urea (23% N) | 5%} | 1.7% Nitrogen |
|  | $KNO_3$ (13.9% N) | 3.8%} |  |
| Potassium | $KNO_3$ (38.7% K) | 3.8% | 1.5% Potassium |
| Phosphorus | $H_3PO_4$ (23.7% P) | 3.4% | 0.8% Phosphorus |
| Zinc | $ZnSO_4$-7 $H_2O$ (36% Zn) | 0.8% | 0.3% Zinc |
| Iron | $FeSO_4$-7 $H_2O$ (31% Fe) | 0.8% | 0.3% Iron |
| Manganese | $MnSO_4$-$H_2O$ (28% Mn) | 0.8% | 0.2% Manganese |
| Vitamin B Cplx | Vitamin B Cplx | 1.0% | 0.04% B-Complex |
| Water | Tap Water | 20.4% | 20.4% Water |

III. Comparative Examples

The above enhanced and standard compositions were compared in a variety of settings

A. Enhancement of Indigenous Microbe Populations

An inactive soil with low microbial activity was treated with 50 gpa Standard Mix and 50 gpa of the Enhanced Mixture and irrigated to incorporate the materials. Approximately 120 hours after treatment soil samples were secured and processed for examination of bacterial populations through dilution plating. Std and Enh are abbreviations for Standard and Enhanced Mix. The following results were observed:

| Treatment | Replications | | | | | Total | Mean |
|---|---|---|---|---|---|---|---|
|  | 1 | 2 | 3 | 4 | 5 |  |  |
| Control | 1.7 | 1.5 | 1.3 | 1.1 | 1.9 | 7.5 | 1.5 a |
| 50 gpa Std | 292.0 | 288.0 | 295.0 | 290.0 | 285.0 | 1,450.0 | 290.0 b |
| 50 gpa Enh | 605.0 | 595.0 | 598.0 | 610.0 | 592.0 | 3,000.0 | 600.0 c |

Populations are expressed in millions of colony forming units per gramn of soil

B. Enhancement of Soil Mineral Release

A relatively sterile soil was first examined for mineral release utilizing distilled water extraction. Portions of the field were then treated with 50 gpa or the standard mix (Std) and 50 gpa of the enhanced composition (Enh) and irrigated to maintain activation of the microbes. Six weeks following treatment, the soil were identically examined for mineral release. Model mineral elements examined were Ca, P and K. The following results were observed:

| Treatment | Calcium | | | Phosphorus | | | Potassium | | |
|---|---|---|---|---|---|---|---|---|---|
| | Before | After | Diff. | Before | After | Diff. | Before | After | Diff. |
| Control | 987 | 1002 | +15 ppm +1.5% | 8 | 8 | 0 0 | 45 | 47 | +2 ppm +4.4% |
| 50 gpa Std | 992 | 1576 | +584 ppm +58.9% | 7 | 17 | +10 ppm +143% | 49 | 97 | +48 ppm +98% |
| 50 gpa Enh | 972 | 2430 | +1458 ppm +150% | 8 | 32 | +24 ppm +300% | 43 | 150 | +107 ppm +249% |

Except for %'s, all data are expressed as ppm mineral in the soil

C. Reductions In Disease Inoculum

Soil heavily infested with sclerotia of the pathogenic fungus, *Verticillium dahliae*, was examined for inoculum levels. Soils were then treated with 50 gpa Std and 50 gpa Enh material in which was mixed approximately 20 trillion colony forming units (cfu's) of beneficial bacteria and fungi, i.e. 1 gallon beneficial microbe suspension (IOTA, sold by FUSION 360, Stockton, Calif.). That is, 50 gpa Std material+1 gallon of beneficial bacteria & fungi were added per acre of soil. Likewise, 50 gpa Enh material+1 gallon of beneficial bacteria & fungi were added per acre of soil. The soil was maintained near 80% field capacity to support microbial activity. Sixty days following the treatment the soils were again examined for inoculum levels of *V dahliae*. The following results were observed:

| Treatment | Replications | | | | T | M |
|---|---|---|---|---|---|---|
| | 1 | 2 | 3 | 4 | | |
| Control Before | 166 | 150 | 168 | 152 | 636 | 159 |
| Control After | 160 | 145 | 174 | 160 | 639 | 160 |
| Difference | −6 | −5 | +6 | +8 | +3 | +1 a |
| 50 Std Bef | 173 | 139 | 165 | 152 | 629 | 157 |
| 50 Std Aft | 65 | 55 | 59 | 61 | 240 | 60 |
| Difference | −108 | −84 | −106 | −91 | −389 | −97 b |
| 50 Enh Bef | 180 | 172 | 166 | 170 | 688 | 172 |
| 50 Enb Aft | 9 | 8 | 5 | 5 | 27 | |
| Difference | −171 | −164 | −161 | −165 | −651 | −165 c |

All cfr's of *Verticillium dahliae* are expressed per gram of soil

D. Reductions In Plant-Parasitic Nematode Populations

A naturally infested vineyard was initially evaluated for plant-parasitic nematode (PPN) populations. Vines were then treated with 50 gpa Std and 50 gpa Enh rates to which were each added 1 gallon of a bacterial-fungal suspension hosting more than 20 trillion cfu's per gallon. Nematode populations were again evaluated at 4 and 8 months. The following results were observed:

| Treatment | Replications | | | | Total | Mean |
|---|---|---|---|---|---|---|
| | 1 | 2 | 3 | 4 | | |
| Control Start | 8,345 | 7,585 | 10,305 | 9,005 | 35,240 | 8,810 |
| Control 4 mos | 11,025 | 7,225 | 8,455 | 12,985 | 39,690 | 9,923 |
| Control 8 mos | 13,220 | 10,250 | 13,325 | 14,120 | 50,915 | 12,729 |
| Overall Change | +4,875 | +2,665 | +3,020 | +5,115 | +15,675 | +3,919 |

-continued

| Treatment | Replications | | | | Total | Mean |
|---|---|---|---|---|---|---|
| | 1 | 2 | 3 | 4 | | |
| 50 Std Start | 10,115 | 9,210 | 8,225 | 11,895 | 39,445 | 9,861 |
| 50 Std 4 mos | 6,125 | 5,350 | 4,035 | 3,980 | 19,490 | 4,873 |
| 50 Std 8 mos | 3,150 | 3,275 | 2,305 | 2,970 | 11,700 | 2,925 b |
| Overall Change | −6,965 | −5,935 | −5,920 | −8,925 | −27,745 | −6,936 |
| 50 Enh Start | 12,845 | 9,205 | 7,995 | 12,430 | 42,475 | 10,619 |
| 50 Enh 4 mos | 345 | 415 | 200 | 190 | 1,150 | 288 |
| 50 Enh 8 mos | 75 | 20 | 15 | nd | 110 | 28 c |
| Overall Change | −12,770 | −9,185 | −7,980 | −12,430 | −42,365 | −10,591 |

All populations are the juvenile stages of Root-Knot Nematode, *Meloidogyne incognita*, per 250 cc of soil E. Increased Water Infiltration Rate A soil with poor textural qualities was measured for water infiltration rate. The method of measurement involved use of a 4" diameter PVC pipe with one end shaped to facilitate each of placement into the soil. The PVC pipe was pushed into the soil to a depth of 4". A volume of water was then added to the cylinder and the rate of infiltration determined. Following initial measurements, the soil was treated with 50 gpa Std and 50 gpa of the Enh material+1 gpa each of a bacterial-fungal suspension which contained more than 20 trillion cfu's per gallon. Material was sprayed evenly over the surface of the soil and gently incorporated with irrigation water. The soil moisture was maintained near 80% field capacity to encourage continuous microbial activity. All plots were again measured for rate of water infiltration 6 weeks following treatment. The following results were obtained:

| Treatment | Replications | | | Total | Mean |
|---|---|---|---|---|---|
| | 1 | 2 | 3 | | |
| Control Before | 0.2 | 0.2 | 0.2 | 0.6 | 0.2 |
| Control After | 0.2 | 0.2 | 0.2 | 0.6 | 0.2 |
| Overall Change | 0 | 0 | 0 | 0 | 0 a |
| 50 Std Before | 0.2 | 0.2 | 0.2 | 0.6 | 0.2 |
| 50 Std After | 0.6 | 0.6 | 0.6 | 1.8 | 0.6 |
| Overall Change | +0.4 | +0.4 | +0.4 | +1.2 | +0.4b |
| 50 Enh Before | 0.2 | 0.2 | 0.2 | 0.6 | 0.2 |
| 50 Enh After | 0.8 | 0.8 | 0.8 | 2.4 | 0.8 |
| Overall Change | +0.6 | +0.6 | +0.6 | +1.8 | +0.6c |

Values represent inches per hour water infiltration rate

F. Increased Root Mass

Bell pepper plants were treated with 50 gpa Std and 50 gpa Enh rates of the material. The treatment was supplemented with 1 gpa of a bacterial-fungal suspension hosting more than 20 trillion cfu's per gallon. Following 3 months of growth, the plants were gently uprooted and the root volume evaluated on a relative scale with the control assigned a value of 1.0. The following results were obtained:

| Treatment | Replications | | | | | Total | Mean |
| --- | --- | --- | --- | --- | --- | --- | --- |
| | 1 | 2 | 3 | 4 | 5 | | |
| Control | 1.0 | 1.0 | 1.0 | 1.0 | 1.0 | 5.0 | 1.0 a |
| 50 gpa Std | 2.5 | 2.5 | 2.5 | 2.5 | 2.5 | 12.5 | 2.5 b |
| 50 gpa Enh | 3.4 | 3.2 | 3.0 | 3.2 | 3.4 | 16.2 | 3.2 c |

Values represent relative root mass of bell peppers in relation to the control

It is evident from the above results and discussion that improved soil amendment compositions that are capable of improving soil in a number of different ways are provided. The compositions are relatively simple and easy to produce. Despite their simplicity, the compositions can provide for significant improvement in terms of soil characteristics, such as texture, water filtration, mineral release and the like. Furthermore, the compositions are useful in reducing the population of soil borne pests and pathogens in the soil. In addition, the compositions are made of natural products that do not pose a health risk to humans or livestock. As such, the subject compositions are a significant advance in the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. An aqueous composition consisting of:
   (a) a predisposing agent;
   (b) a carbon-skeleton-energy component;
   (c) a vitamin-cofactor and
   (d) water;
   wherein said composition does not include nitrogen, phosphorous, zinc, iron or manganese.

2. The composition according to claim 1, wherein said carbon-skeleton-energy component comprises $C_2$ to $C_{10}$ molecules or polymers thereof.

3. The composition according to claim 1, wherein said predisposing agent is a lignosulfonate.

4. The composition according to claim 1, wherein said predisposing agent is gallic acid.

5. The composition according to claim 1, wherein said predisposing agent is lignosulfonate and gallic acid.

6. An aqueous composition consisting of:
   (a) a carbon-skeleton-energy component;
   (b) a lignosulfonate;
   (c) gallic acid;
   (d) a vitamin-cofactor; and
   (e) water
   wherein said composition does not include nitrogen, phosphorous, zinc, iron or manganese.

7. The composition according to claim 6, wherein said carbon-skeleton-energy component is a molasses.

8. The composition according to claim 1, wherein said vitamin-cofactor is yeast extract.

9. The composition according to claim 6, wherein said carbon-skeleton-energy component is from about 10 to 50% w/w of said composition.

10. The composition according to claim 6, wherein said lignosulfonate is from about 10 to 50% w/w of said composition.

11. The composition according to claim 6, wherein said gallic acid is from about 0.001% to 10% w/w of said composition.

12. The composition according to claim 6, wherein said vitamin-cofactor is from about 0.001 to 10% w/w of said composition.

13. An aqueous composition consisting of:
   (a) from about 10 to 50% w/w of a molasses;
   (b) from about 10 to 50% w/w of a lignosulfonate;
   (c) from about 0.001 to 10% w/w of gallic acid;
   (d) from about 0.001 to 10% w/w of yeast extract; and
   (e) water
   wherein said composition does not include nitrogen, phosphorous, zinc, iron or manganese.

14. The composition according to claim 13, wherein said molasses makes up from about 30 to 40% w/w of said composition.

15. The composition according to claim 13, wherein said lignosulfonate makes up from about 30 to 40% w/w of said composition.

16. The composition according to claim 1, wherein said gallic acid makes up from about 0.01 to 1.0% w/w of said composition.

17. The composition according to claim 13, wherein said yeast extract makes up from about 2 to 3% w/w of said composition.

18. The composition according to claim 13, wherein said water makes up from about 20 to 30% w/w of said composition.

19. A method for amending soil, said method comprising:
   applying to said soil an aqueous composition consisting of:
   (a) from about 10 to 50% w/w of a molasses;
   (b) from about 10 to 50% w/w of a lignosulfonate;
   (c) from about 0.001 to 10% w/w of gallic acid;
   (d) from about 0.001 to 10% w/w of yeast extract; and
   (e) water
   wherein said composition does not include nitrogen, phosphorous, zinc, iron or manganese.

* * * * *